United States Patent
Meixner et al.

(10) Patent No.: US 10,292,871 B2
(45) Date of Patent: May 21, 2019

(54) WOUND CARE SYSTEM WITH A MAT OF CAPILLARY MEMBRANES

(71) Applicant: 3M INNOVATIVE PROPERTIES COMPANY, St. Paul, MN (US)

(72) Inventors: Carsten Meixner, Huckeswagen (DE); Haythem Korbi, Wuppertal (DE)

(73) Assignee: 3M Innovative Properties Company, St. Paul, MN (US)

( * ) Notice: Subject to any disclaimer, the term of this patent is extended or adjusted under 35 U.S.C. 154(b) by 219 days.

(21) Appl. No.: 15/036,195

(22) PCT Filed: Nov. 12, 2014

(86) PCT No.: PCT/EP2014/074312
§ 371 (c)(1),
(2) Date: May 12, 2016

(87) PCT Pub. No.: WO2015/071280
PCT Pub. Date: May 21, 2015

(65) Prior Publication Data
US 2016/0287446 A1    Oct. 6, 2016

(30) Foreign Application Priority Data
Nov. 13, 2013   (EP) .................................... 13192648

(51) Int. Cl.
*A61F 13/00* (2006.01)
*B01D 69/08* (2006.01)
(Continued)

(52) U.S. Cl.
CPC .. *A61F 13/00068* (2013.01); *A61F 13/00012* (2013.01); *A61F 13/00017* (2013.01);
(Continued)

(58) Field of Classification Search
CPC .......... A61F 13/00017; A61F 13/00029; A61F 13/00068; A61F 13/00012;
(Continued)

(56) References Cited

U.S. PATENT DOCUMENTS

| 4,382,441 A * | 5/1983 | Svedman .......... A61F 13/00068 604/114 |
| 5,141,031 A | 8/1992 | Baurmeister |
| 5,549,584 A | 8/1996 | Gross |
| 6,410,307 B1 | 6/2002 | Glockner |
| 6,497,752 B1 | 12/2002 | Kessler |
| 9,321,013 B2 | 4/2016 | Bornemann |

(Continued)

FOREIGN PATENT DOCUMENTS

| DE | 28 33 493 | 2/1980 |
| DE | 38 39 567 | 6/1990 |

(Continued)

OTHER PUBLICATIONS

OA for U.S. Appl. No. 16/036,142 dated Jun. 25, 2018 (17 pages).
Final Rejection for U.S. Appl. No. 16/036,142 dated Jan. 2, 2019 (14 pages).

*Primary Examiner* — Tatyana Zalukaeva
*Assistant Examiner* — Gabriella Burnette
(74) *Attorney, Agent, or Firm* — Scott A. Baum

(57) ABSTRACT

A wound care system comprising a single-layer arrangement of mutually parallel capillary membranes with a porous, semi-permeable wall, a lumen and at least one open end. The capillary membranes are connected to one another by connection elements to form a mat and are held at a distance from one another by the connection elements.

9 Claims, 4 Drawing Sheets

Figure 1:
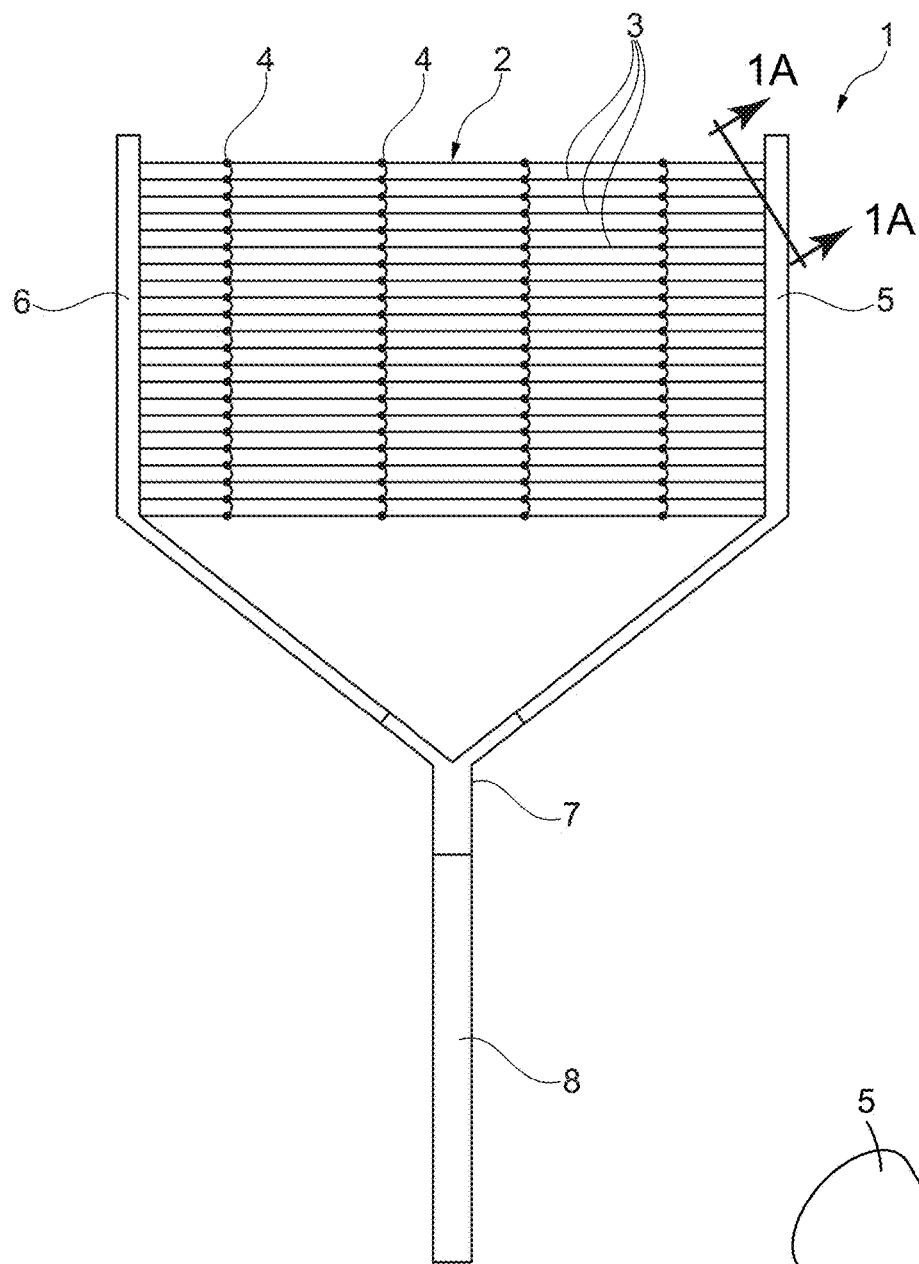
Figure 1A:
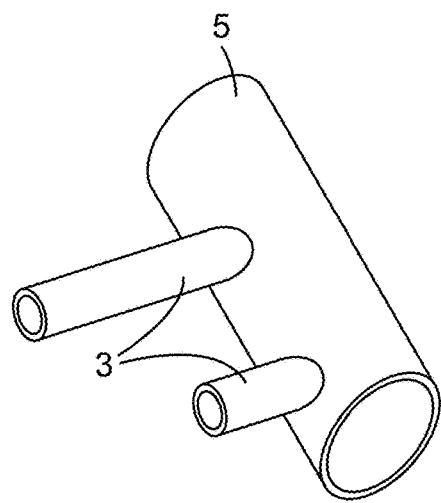

(51) Int. Cl.
  *A61M 3/02* (2006.01)
  *A61M 1/00* (2006.01)
  *A61M 35/00* (2006.01)
  *B01D 63/02* (2006.01)
  *B01D 65/02* (2006.01)

(52) U.S. Cl.
  CPC .. *A61F 13/00025* (2013.01); *A61F 13/00042* (2013.01); *A61M 1/0084* (2013.01); *A61M 1/0088* (2013.01); *A61M 3/0283* (2013.01); *B01D 63/026* (2013.01); *B01D 65/022* (2013.01); *B01D 69/081* (2013.01); *A61F 2013/00548* (2013.01); *A61M 1/0037* (2013.01); *A61M 35/00* (2013.01)

(58) Field of Classification Search
  CPC .......... A61F 13/00021; A61F 13/00042; A61F 2013/0017; A61F 2013/00548; A61M 1/0084; A61M 1/0037; A61M 1/0088; A61M 35/00
  See application file for complete search history.

(56) References Cited

U.S. PATENT DOCUMENTS

| | | | |
|---|---|---|---|
| 9,907,708 B2 | 3/2018 | Riesinger | |
| 10,039,673 B2 | 8/2018 | Mumby | |
| 2009/0191631 A1 | 7/2009 | Bornemann | |
| 2009/0196855 A1* | 8/2009 | Bornemann | A61M 1/0084 424/93.7 |
| 2012/0215193 A1 | 8/2012 | Siniaguine | |
| 2013/0023842 A1 | 1/2013 | Song | |

FOREIGN PATENT DOCUMENTS

| | | |
|---|---|---|
| DE | 43 08 850 | 9/1994 |
| DE | 102 21 565 | 12/2003 |
| DE | 102009039868 | 3/2011 |
| EP | 0 299 381 | 1/1989 |
| WO | WO 2007/116072 | 10/2007 |
| WO | WO 2008/106515 | 9/2008 |
| WO | WO 2010/037092 | 4/2010 |
| WO | WO 2013/066426 | 5/2013 |

* cited by examiner

WOUND CARE SYSTEM WITH A MAT OF CAPILLARY MEMBRANES

CROSS REFERENCE TO RELATED APPLICATIONS

This application is a national stage filing under 35 U.S.C. 371 of PCT/EP2014/074312, filed Nov. 12, 2014, which claims the benefit of European Patent Application No. 13192648.7, filed Nov. 13, 2013, the disclosures of which are incorporated by reference in their entirety herein.

The invention relates to a wound care system for introduction into a wound or for application to a skin wound and under a wound bandage, comprising a single-layer arrangement of mutually parallel capillary membranes with a porous, semi-permeable wall and a lumen and at least one open end, wherein the capillary membranes have an external diameter in the range of 50 to 5000 μm and a wall thickness in the range of 5 to 1000 μm, and wherein the capillary membranes, with their at least one open end, are fluidically connected to at least one common supply line with a wall and a lumen, so that fluids, media, gases and/or other substances can be conveyed through the supply line and the capillary membranes.

The aim of modern wound care is to create a moist environment for wound care which promotes the processes taking place during healing. Depending on the healing phase, modern active wound dressings must therefore be capable of discharging large amounts of exudate or of keeping the wound moist. In wound care, it is important to provide an improved liquid/material exchange for the introduction of factors/medications into the wound and/or for an improved removal of liquid/secretion and/or material from the wound. Applications include the use of such wound dressing systems in a soft tissue wound, in an abdominal wound and on a skin wound.

A method and a device for removing secretions or exudate from wounds is commercially known as V.A.C.® Therapy System (from KCI, USA). This system provides for an alternating introduction of liquid into the wound and a subsequent, hence also alternating and thus non-continuous, removal of liquid from the wound. A foam material introduced into the wound, which exerts forces on the wound at negative pressure, is intended to promote wound healing in this system.

DE 10 2006 042 732 describes a capillary membrane system for wound care in which the wound is perfused and supplied via a hollow membrane arrangement consisting of up to 1000 hollow fibers having at least one common supply line and at least one common discharge line in the context of perfusing a capillary bed, and which should make possible perfusion with an antibiotic and growth factor. This should make possible uniform material distribution under continuous perfusion, even when a moderate vacuum is created. DE 10 2006 042 732 explains that additional capillary membrane systems are advantageous for optimum supply and disposal.

Although progress in wound care has already been made with the capillary membrane system described in DE 10 2006 042 732, there is a continued need for simple and efficient wound care systems with which the processes necessary for wound care, such as flushing and disinfecting, can be carried out without removing bandages, which, if necessary, make possible nutrient supply, electrolyte replacement and/or detoxification or even growth factor supply or supply with antibiotics, and which facilitate easy and safe handling.

The problem of the present invention is that of providing such a wound care system.

The problem is solved by a wound care system which comprises a single-layer arrangement of mutually parallel capillary membranes having a porous, semi-permeable wall and a lumen and at least one open end,
   wherein the capillary membranes have an external diameter in the range of 50 to 5000 μm and a wall thickness in the range of 5 to 1000 μm,
   wherein the capillary membranes, with their at least one open end, are connected to at least one common supply line having a wall and a lumen, so that fluids, media, gases and/or other substances can be conveyed through the supply line and the capillary membranes, and
   wherein the supply line is connectable to a supply unit or a disposal unit, characterized in that
   the capillary membranes, with their at least one open end, are embedded so fluid-tightly in the wall of the at least one common supply line at its outer periphery that a fluid connection exists between the lumen of the supply line and the lumen of the capillary membranes,
   the arrangement of mutually parallel capillary membranes furthermore has a plurality of spaced and mutually parallel connection elements by means of which the capillary membranes are connected to one another to form a mat and are held at a distance from one another by the connection elements,
   the distance of the capillary membranes from one another in the mat is 1 to 10 times the external diameter of the capillary membranes, wherein the distance is measured from the longitudinal axes of the capillary membranes, and
   the distance of the connection elements from one another lies in the range of 1 to 50 mm.

It has been shown that such a wound care system makes possible nearly homogenous supply to a wound, e.g., with nutrient solution, and also nearly homogenous disposal from a wound, e.g., of exudate, wherein, at the same time, the configuration of the wound care system facilitates easy and safe handling. To that end, the wound care system can be inserted into the wound and be covered, e.g., with a semi-occlusive transparent film to protect the wound from drying out or from infection. The at least one supply line then exits from the wound area under the film and is connected, e.g., via a pump, to a supply unit for, e.g., a nutrient solution, e.g., a nutrient solution reservoir. The arrangement of the capillary membranes can also be used to suction exudate from the wound. In this case, the at least one supply line is connected to a disposal unit, in particular a vacuum unit.

Supplying the wound with a liquid and suctioning the exudate from the wound can also be carried out intermittently via the arrangement of the capillary membranes by connecting the at least one supply line, for example via a T-piece, to a liquid reservoir via a first sub-line, and to a vacuum unit via a second sub-line. Liquids can be supplied or exudate can be suctioned off at predetermined time intervals by means of controllable shut-off valves.

In one embodiment, the wound care system can furthermore comprise a pouch-shaped wound dressing, wherein the pouch-shaped wound dressing is closed at its outer edge and has an upper face, a lower face and a pouch interior, wherein the lower face and the upper face are each formed from a two-dimensional material and the lower face is permeable to fluids, wherein the arrangement consists of mutually parallel capillary membranes in the pouch interior and wherein the at least one supply line is connectable to a supply unit or a disposal unit outside the pouch-shaped wound dressing.

The pouch-shaped wound dressing with the wound care system can be inserted into a wound to be treated, such that the bottom face is in contact with the wound. The wound can be fed with fluid by means of the wound care system, e.g. in the form of a nutrient solution which spreads in the pouch after discharge from the capillary membranes and is delivered to the wound through the semi-permeable lower face of the pouch bottom. The wound care system can then be connected via the at least one supply line, e.g. via a pump, to a supply unit for the liquid, e.g., a reservoir for the nutrient solution.

The pouch-shaped wound dressing can preferably be designed in such a way that the connection of the arrangement of mutually parallel capillary membranes or capillary membranes with the at least one supply line is located in the pouch interior, and that the at least one supply line exits from the pouch-shaped wound dressing via a through-opening, fluid-tightly fitted to its external cross-section. The connection of the arrangement of mutually parallel capillary membranes or capillary membranes with the at least one supply line may likewise be arranged outside the pouch-shaped wound dressing on the upper face and the arrangement of mutually parallel capillary membranes for connecting the at least one supply line may exit from the pouch-shaped wound dressing via a fluid-tight through-opening. Essential features of the wound care system are that, because of the mat-like construction, the capillary membranes are kept at a uniform distance from one another by being held by the connection elements, and that the capillary membranes are present in the mat in such a concentration that the distance of the capillary membranes from one another in the mat is 1 to 10 times the external diameter of the capillary membranes, wherein the distance is measured from the longitudinal axes of the capillary membranes. For this purpose, those mats are preferred in which the distance of the capillary membranes from one another in the mat is 1.05 to 6 times the external diameter of the capillary membranes. Distances of the capillary membranes from one another in the mat in the range of 1.05 to 3 times the external diameter of the capillary membranes are particularly preferred. In a further particularly preferred embodiment, distances of the capillary membranes from one another in the mat are more than 1.5 times the external diameter of the capillary membranes. It has been found that sure separation of the capillary membranes from one another can be achieved in this way.

At the same time, with an eye to good homogeneous supply of the wound to be treated, it is important in the arrangement of the capillary membranes that the capillary membranes are connected to one another by means of a plurality of spaced and mutually parallel connection elements to form a mat and that they are held at a distance from one another by the connection elements. The connection elements are at a defined distance from one another, which is preferably in the range of 1 to 50 mm, a distance in the range of 3 to 20 mm being particularly preferred, and a distance in the range of 4 to 6 mm being most suitable. In fact, it has been shown that the points of contact between the capillary membranes and the connection elements, for example when supplying the wound to be treated with a nutrient solution, for example, significantly promote the distribution of the liquid over the area of the capillary membrane arrangement. Hence, it has been observed that discharge of liquid from the capillary membranes at the points of contact is favored.

The capillary membranes preferably have an external diameter in the range of 200 to 1500 μm. Likewise preferred are capillary membranes having a wall thickness in the range of 20 to 400 μm, their external diameter preferably lying in the above-mentioned ranges.

In one design of the wound care system, the arrangement of the capillary membranes is designed to feed or discharge liquid media. In order to then ensure a uniform supply to and disposal from the wound, in a preferred embodiment, the capillary membranes are highly permeable to liquids. In this case, transmembrane flow of water in the capillary membranes preferably lies in the range of 0.01 to 50 mL(min·cm$^2$·bar).

Naturally, the number of capillary membranes in the arrangement of the capillary membranes of the wound care system depends primarily on the size of the wound care system and thus on the size of the capillary membrane arrangement, which, in turn, must be adjusted to the size of the wound to be treated. The arrangement of the capillary membranes can therefore be composed of about 10 to several hundred or thousand mutually parallel capillary membranes.

The mutually parallel capillary membranes are embedded at their outer periphery so fluid-tightly at least one of their ends in the wall of the at least one supply line that a fluid connection exists between the lumen of the supply line and the lumen of the capillary membranes and that liquids, media, gases and/or other substances can be conveyed through the supply line and the capillary membranes.

The at least one supply line is preferably open at its one end and connectable to a supply unit or a disposal unit, whereas the other end of the at least one supply line is closed. The embedding can be accomplished by means of conventional adhesives, such as, e.g., curable silicone materials, polyurethane resins or epoxy resins. Curable silicone materials are preferably used because of their superior flexibility. If the capillary membranes are embedded in a supply line with only one of their ends, the other, opposite, end of the capillary membrane is closed by fusing or bonding, for example. The capillary membranes can also be open at both of their ends and embedded in a supply line with both of these ends on one side of the arrangement, wherein the capillary membranes are then designed to be U-shaped at their free end and are thus closed there. In those cases, the capillary membranes are operated in the dead-end mode.

In particular with wider wound care systems, an embodiment of the single-layer capillary membrane arrangement is advantageous, in which the mutually parallel capillary membranes are open at both of their ends, and the opposite ends of which are embedded in a respective supply line, wherein the supply lines are then preferably located on opposite sides of the capillary membrane arrangement. In this case, as well, embedding is effected in such a way that the capillary membranes are fluid-tightly embedded at the outer periphery and create a fluid connection between the lumen of the respective supply line and the lumen of the capillary membranes. Such an embodiment having two supply lines makes supply and/or disposal in the cross-flow mode possible via the capillary membrane arrangement. However, when operating the capillary membrane arrangement in the dead-end mode, in particular with wider capillary membrane arrangements, for good homogeneity of the supply or disposal across the wound area, it may also be advantageous if the capillary membrane arrangement has a supply line at both ends of the capillary membranes.

The diameter of the at least one supply line primarily conforms to the external diameter of the capillary membranes embedded in it. The at least one supply line therefore preferably has an internal diameter in the range of 0.1 to 10 mm. It is likewise preferred if the wall thickness of the flexible silicone tube ranges from 0.1 to 5 mm. In the event that a supply line with a non-circular cross-section is used, the equivalent diameter d=4A/U of the internal cross-section is used as the internal diameter, where A is the area of the internal cross-section and U its circumference. For example, the internal cross-section of the supply line may also be oval, or approximately square or rectangular. For the at least one supply line, a silicone tube through the walls of which the capillary membrane ends pass and into which they are glued has proven to be suitable, for example. Preferably, the at least one common supply line is a flexible silicone tube. Embedding or bonding in the wall of the supply line can be accomplished by means of conventional adhesives, such as, e.g., curable silicone materials, polyurethane resins or epoxy resins.

According to the invention, the mutually parallel capillary membranes are connected to one another by means of spaced and mutually parallel connection elements and are held at a distance from one another by the connection elements, wherein the connection elements touch the capillary membranes at their outer periphery or entwine with the capillary membranes. Along their longitudinal extension, the connection elements do not have any closed flow channels and consequently fluids cannot flow through along their longitudinal extension. The connection elements can run transversely to the mutually parallel capillary membranes or also at a different angle. The connection elements can also be adhesive strips or, for example, strand-like elements made of a silicone material. In a preferred embodiment, the capillary membranes are connected to form a mat by means of thread-like connection elements. The connection elements are particularly preferably multifilament textile threads. Multifilament polyester threads, polypropylene threads or polytetrafluoroethylene threads have proven to be particularly successful multifilament textile threads. Most suitable are hydrophilic threads, preferably those made of polyester. As explained, it has been shown that connection elements thusly designed have a supporting effect in the distribution of liquids fed to the wound.

In a preferred embodiment, the capillary membrane mat can be a knitted mat in which the capillary membranes and the connecting fibers are knitted together, and in which the capillary membranes run transverse to the extension direction of the capillary membrane mat and in which the length of the capillary membranes is determined by the width of the mat. In a further preferred embodiment, the capillary membrane mat can be a woven mat in which the capillary membranes and the connecting fibers are woven together and in which the capillary membranes run in the extension direction or the running direction of the capillary membrane mat, and the textile fibers run transverse thereto. Knitted and woven capillary membrane mats, as well as ways of producing them, are described, for example, in DE 38 39 567, in DE 43 08 850 and in EP 0 442 147. Mats can be produced in a simple manner in particular by means of knitting technology where the capillary membranes are designed in a U-shape at their free ends and closed off there. Such mats can be produced by depositing a meandering capillary membrane in mutually parallel strands, which are connected by the knitting fibers. After the knitted mats have been completed, the U-shaped ends are severed on at least one side of the knitted mat, and the resulting open ends of the capillary membranes are then embedded in the at least one supply line. In the event that the U-shaped ends are severed on both sides of the knitted mat, the resulting opposite open ends are embedded in respective supply lines.

The two-dimensional extension of the single-layer arrangement of mutually parallel capillary membranes can have any shape, as far as this is possible for arrangements of mutually parallel capillary membranes. In its simplest embodiment, the arrangement of mutually parallel capillary membranes is square or rectangular in shape. For example, in arrangements where the capillary membranes are embedded in a supply line with only one of their ends, it is possible, however, that an arc-shaped contour is formed, for example by an appropriately adapted end-fusing of the free, closed ends of the mutually parallel capillary membranes. It is likewise possible that the arrangement of mutually parallel capillary membranes also has, e.g., a trapezoidal contour.

In principle, all prior art organic polymers suitable for the formation of capillary membranes may be considered as materials for the capillary membranes, wherein said polymers must have good biocompatibility. Moreover, it is also required that the membrane polymer allows for sterilization of the wound dressing system, for example by steam sterilization, sterilization by γ-irradiation or sterilization by means of ethylene oxide. For this purpose, the organic polymers may be natural polymers or synthetically produced polymers. Natural polymers in particular are those based on cellulosic polymers, which likewise includes polymers that have been subjected to so-called polymer-analogous reactions. Examples of polymers based on cellulose are those from regenerated cellulose, cellulose acetate or modified cellulose, such as, e.g., cellulose esters, cellulose ethers, cellulose modified with benzyl groups (benzyl cellulose) or cellulose modified with dimethylaminoethyl or mixtures of these cellulosic polymers. Furthermore, polymers based on chitin or chitosan may also be used.

As synthetically produced polymers, i.e. synthetic polymers, those consisting of polyolefins, polyamides, polyacrylonitriles, polycarbonates, polyesters or sulfone polymers, and modifications, blends, mixtures or copolymers of these polymers obtained therefrom can be used. Preferably, those polymers are used which are based on sulfone polymers, such as, in particular, polysulfone or polyether sulfone. Further polymers may be admixed as additives to the synthetic polymers, such as, e.g., polyethylene oxide, polyhydroxy ether, polyethylene glycol, polyvinyl alcohol or polycaprolactone. In addition, the capillary membranes may also be coated with an additive. Such capillary membranes preferably contain a hydrophilizing agent, e.g., polyvinylpyrrolidone, or hydrophilic modifications of these polymers, as well.

These capillary membranes can be modified with a view to specific applications, e.g. via coupling of functional groups, or be coated, for example, with heparin or one or more antibiotics.

In addition to the single-layer arrangement of mutually parallel capillary membranes, the wound care system may comprise further components, such as, e.g., at least one additional arrangement of capillary membranes in which the capillary membranes of the additional arrangement are membranes for oxygenation, i.e., membranes with which it is possible to feed oxygen to the wound. Such membranes are disclosed, for example, in EP-A-1 144 096, EP-A-0 299 381 or DE-A-28 33 493. The combination with an additional mat-like arrangement of semi-permeable capillary membranes is also possible, so that, e.g., a first arrangement of capillary membranes can supply the wound with growth factors or antibiotics, and the additional arrangement can control temperature or regulate pH. In this case, the respective mat-like capillary arrangements can be superimposed on each other. However, it is also possible that two different capillary membranes are interconnected to form a mat, wherein the different capillary membranes are embedded with their ends in different supply lines, which are preferably arranged on opposite sides of the mat. Such mats can be obtained, for example, by knitting together offset meandering capillary membranes in which the U-shaped bends of the capillary membranes are located at different positions across the width of the mat. By cutting the respective outer U-shaped bends, the capillary membranes are opened on only one side of the mat and can be there embedded in a supply line.

In addition to the single-layer arrangement of mutually parallel capillary membranes, the wound care system may also comprise a drainage system, for example, by means of which it is possible to discharge the exudate separately. In one embodiment, the wound care system may comprise a suctioning sponge equipped with an exudate discharge line. The drainage system may also be designed as an additional capillary membrane mat, but it may also be in the form of a drainage catheter, which may be a section of tubing, for example made of a silicone material, or a small tube. Such a drainage catheter can have wall perforations, through which, e.g., exudate can be suctioned from the wound or from the interior of the pouch-shaped wound dressing and from the wound after connecting the drainage catheter to a vacuum unit.

In the event that the wound care system also comprises a pouch-shaped wound dressing in which the arrangement of mutually parallel capillary membranes is arranged, the at least one arrangement of mutually parallel capillary membranes extends two-dimensionally into the interior of the pouch. The dimensions of the arrangement of mutually parallel capillary membranes result from their external measurements in the two-dimensional extension. With regard to its two-dimensional extension, the arrangement of the capillary membranes preferably fills at least 20% and particularly preferably at least 50% of the two-dimensional extension of the interior of the pouch of the pouch-shaped wound dressing. With regard to its two-dimensional extension, it is particularly advantageous if the arrangement of the capillary membranes fills at least 70% of the two-dimensional extension of the interior of the pouch of the pouch-shaped wound dressing, wherein fill ratios in the range of 90% can also be achieved. It is advantageous if the arrangement of the capillary membranes is centrally arranged in the pouch-shaped wound dressing.

The pouch-shaped wound dressing may have any contour. Preferably, however, the contour is round, oval, square or rectangular. The lower and upper faces of the pouch-shaped wound dressing are connected, for example by fusing or bonding, at the outer margin or the outer edges of the wound dressing. Cured silicone strips, among other things, are suitable for bonding. For rectangular or square pouch-shaped wound dressings, the planar capillary membrane system arranged therein preferably also has a rectangular or square contour. For round or oval pouch-like wound dressings, the at least one planar capillary membrane system contained therein is conveniently also designed to be square or rectangular, wherein, with regard to dimensions, the previously specified dimensions apply. However, it may also be fitted to the contour of the pouch-like wound dressing, for example by appropriately adapted end-fusing of the non-embedded ends of the capillary membranes in an arrangement of the capillary membranes having only one supply line, resulting in an arched contour at this edge of the arrangement of the capillary membranes.

The lower face of the pouch-shaped wound dressing is permeable to fluids. In this connection, the lower face, for example, may consist of a nonwoven, two-dimensional material, a grid-like or web-like material, a perforated film or a semi-permeable microporous flat membrane. In an advantageous embodiment, the lower face consists of a nonwoven two-dimensional material or a semi-permeable microporous flat membrane. The lower face preferably has a water permeability of at least 0.01 mL/(min·cm$^2$·bar) and particularly preferably at least 10 mL/(min·cm$^2$·bar). A lower face having a water permeability of at least 500 mL/(min·cm$^2$·bar) has been found to be most successful.

For applications of the wound dressing system in which the wound is not only supplied with liquid via the wound dressing system, but in which disposal is also carried out, i.e., a discharge of liquids from the wound and, in particular, a disposal of exudate, it is advantageous if the lower face has openings, the openings preferably having a diameter of at least 100 μm. Opening diameters of no more than 10 mm are preferred and particularly preferred are those of no more than 5 mm. In the event that the lower face consists of a semi-permeable microporous flat membrane, in a preferred embodiment said membrane additionally has openings, e.g., in the form of perforations. If the openings have a non-circular contour, the equivalent diameter $D=4A/U$ of the opening is used as the diameter, where A is the area of the respective opening and U its circumference. The openings may be distributed regularly or irregularly over the area of the lower face, wherein a regular homogeneous distribution is preferred. In this connection, the distance between the openings may lie in the range of 1 to 20 mm, measured from the outer edge of the opening.

The lower and upper faces of the pouch-shaped wound dressing may consist of the same or different materials. However, whereas the lower face is always permeable to fluids, the upper face is preferably made of a preferably film-like material impermeable to fluids which is fluid-tightly connected at its side edge(s) to the lower face so as to be impermeable to fluids. The upper face may also be a semi-permeable microporous flat membrane. In this case, however, the upper face has a lower permeability to fluids than the lower face, so that, when in use, the distribution of liquid fed to the lower face of the pouch-shaped wound dressing, and thus towards the wound, is ensured. In the event that the lower and upper faces are the same or are made of semi-permeable microporous flat membrane of the same permeability, the lower face has perforations.

As materials for the lower or upper face of the pouch-shaped wound dressing, the same organic polymers which were specified earlier as polymers for the capillary membranes and which can be processed to flat films or flat membranes can in principle be considered. Preferably, the lower and/or the upper face of the pouch-shaped wound dressing are composed of polyolefins, polyamides, polyacrylonitriles, polycarbonates, polyesters or sulfone polymers, and modifications, blends, mixtures or copolymers of these polymers obtained therefrom. Particularly preferably, the lower and upper faces comprise sulfone polymers, wherein polysulfone or polyether sulfone are most suitable.

In the event that the wound care system comprises a pouch-shaped wound dressing, a drainage system can be arranged in the interior of the pouch which is suitable for removing exudate from wounds being treated.

The drainage system may preferably be at least one drainage catheter which exits from the pouch-shaped wound dressing via a through-opening, fluid-tightly fitted to its cross-section, and is connectable to a vacuum unit so as to create a vacuum inside the pouch interior when in use. The at least one drainage catheter can be a piece of tubing, for example of a silicone material, or a small tube which is arranged in the interior of the pouch of the wound dressing and which exits from the wound dressing via the through-opening. The segment located in the interior of the pouch-shaped wound dressing of the at least one drainage catheter preferably has wall perforations through which, after connecting the at least one drainage catheter to a vacuum unit, exudate, e.g., can be suctioned from the wound or from the interior of the pouch-shaped wound dressing and from the wound. The at least one drainage catheter preferably has an internal diameter in the range of 0.1 to 15 mm and a wall thickness in the range of 0.1 to 3 mm and preferably extends across at least the entire length or width of the pouch interior. The drainage catheter can also have a non-circular cross-section. In this case, the equivalent diameter $d_D = 4A_D/U_D$ of the internal cross-section is used as the internal diameter, where $A_D$ is the area of the internal cross-section of the drainage catheter and $U_D$ is its circumference.

The characterizations of the properties of the capillary membranes or flat membranes used in the wound dressing system are based on the following measurement methods:

Transmembrane Flow (Water Permeability) for Capillary Membranes:

A test cell having a defined capillary membrane number and length is produced from the capillary membranes to be tested. For this, the capillary membranes are embedded at their ends at both sides in a polyurethane resin. After the resin has cured, the embeddings are cut to a length of about 30 mm, the cut thus opening the lumens of the capillary membranes. The capillary lumens in the embeddings must be checked for permeability. The free length of the capillary membranes between the embeddings is typically 120+/−10 mm. The number of capillary membranes should be calculated such that a filtration area of 30 cm$^2$ is provided in the test cell, taking into account the free length and the internal diameter of the capillary membranes.

The test cell is integrated into a test apparatus and perfused with ultrafiltered and deionized water set to 25° C. at a defined test pressure (about 0.4 bar). The filtered amount of water obtained during a measuring time of 2 min, i.e., the permeate produced during the measurement, is gravimetrically or volumetrically determined. Before starting the measurement, air must be purged from the system. To determine the TMF, the test apparatus measures the inlet and outlet pressure at the test cell. The measurement is carried out at 25° C.

The transmembrane flow, TMF, is determined according to formula (I).

$$TMF = \frac{V_w}{\Delta t \cdot A_M \cdot \Delta p}\left[\frac{\text{ml}}{\text{cm}^2 \cdot \text{min} \cdot \text{bar}}\right] \quad (I)$$

Where:
$V_w$=water volume [mL] perfused through the membrane sample during the measuring time
$\Delta t$=measuring time [min]
$A_M$=perfused area of the membrane sample (typically 30 cm$^2$)
$\Delta p$=pressure set during the measurement [bar]

Permeability to Water of the Lower Face of the Pouch-Shaped Wound Dressing:

Disk-shaped samples to be tested are punched out of the two-dimensional material of the lower face of the pouch-shaped wound dressing and clamped at the circumference in a suitable sample holder so fluid-tightly that a free measuring area of 17.35 cm$^2$ results. The sample holder is located in a housing that can be perfused by pressurized water. The clamped sample is then perfused with deionized water set to 25° C. at a defined pressure of between 0.1 and 0.2 bar. The water volume perfused through the sample during a measuring time of 60 s is gravimetrically or volumetrically determined.

The permeability to water, $TMF_W$, is determined according to formula (II).

$$TMF_W = \frac{V_w}{\Delta t \cdot A_M \cdot \Delta p}\left[\frac{\text{ml}}{\text{cm}^2 \cdot \text{min} \cdot \text{bar}}\right] \quad (II)$$

Where:
$V_w$=water volume [mL] perfused through the sample during the measuring time
$\Delta t$=measuring time [min]
$A_M$=perfused area of the sample (typically 17.35 cm$^2$)
$\Delta p$=pressure set during the measurement [bar]

Figure 2:
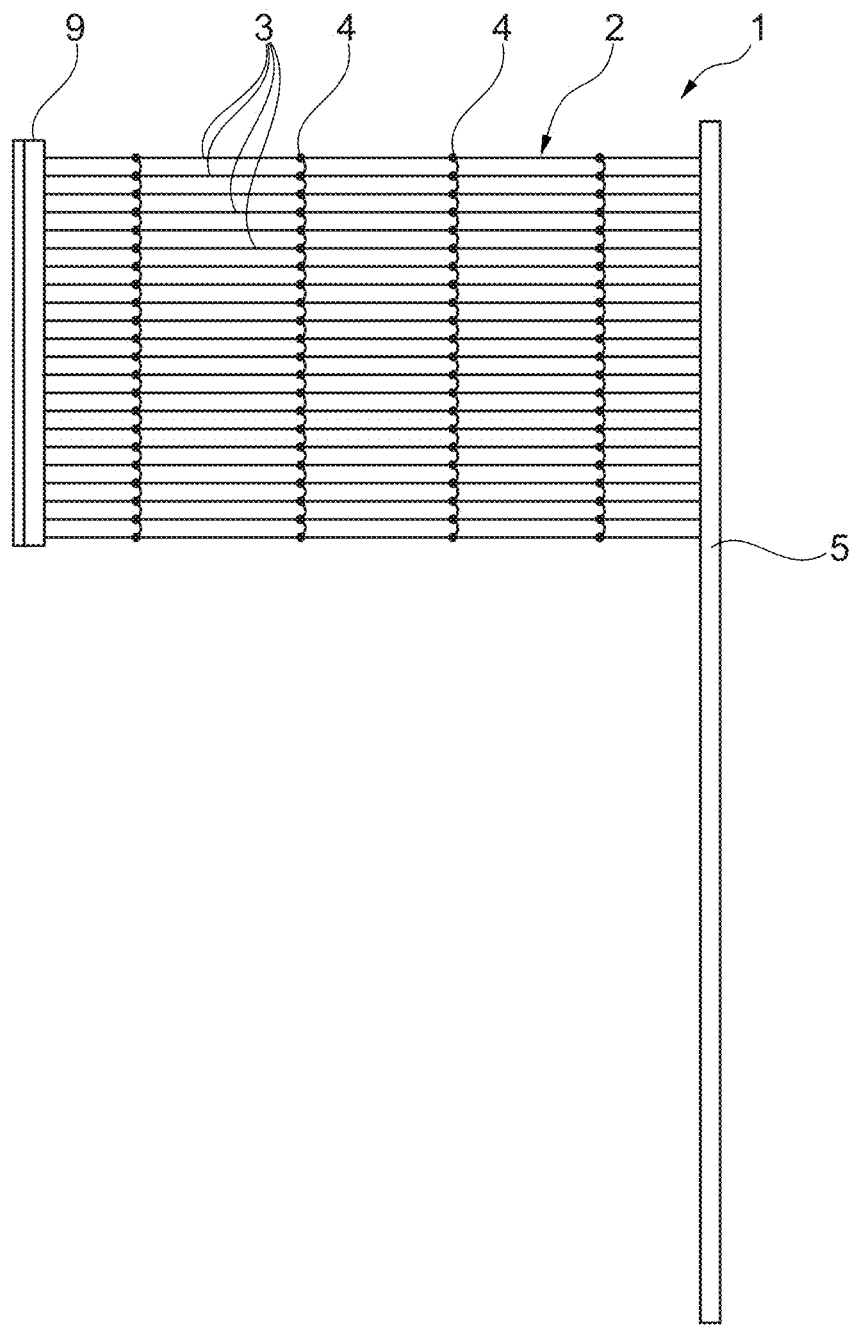
Figure 3:
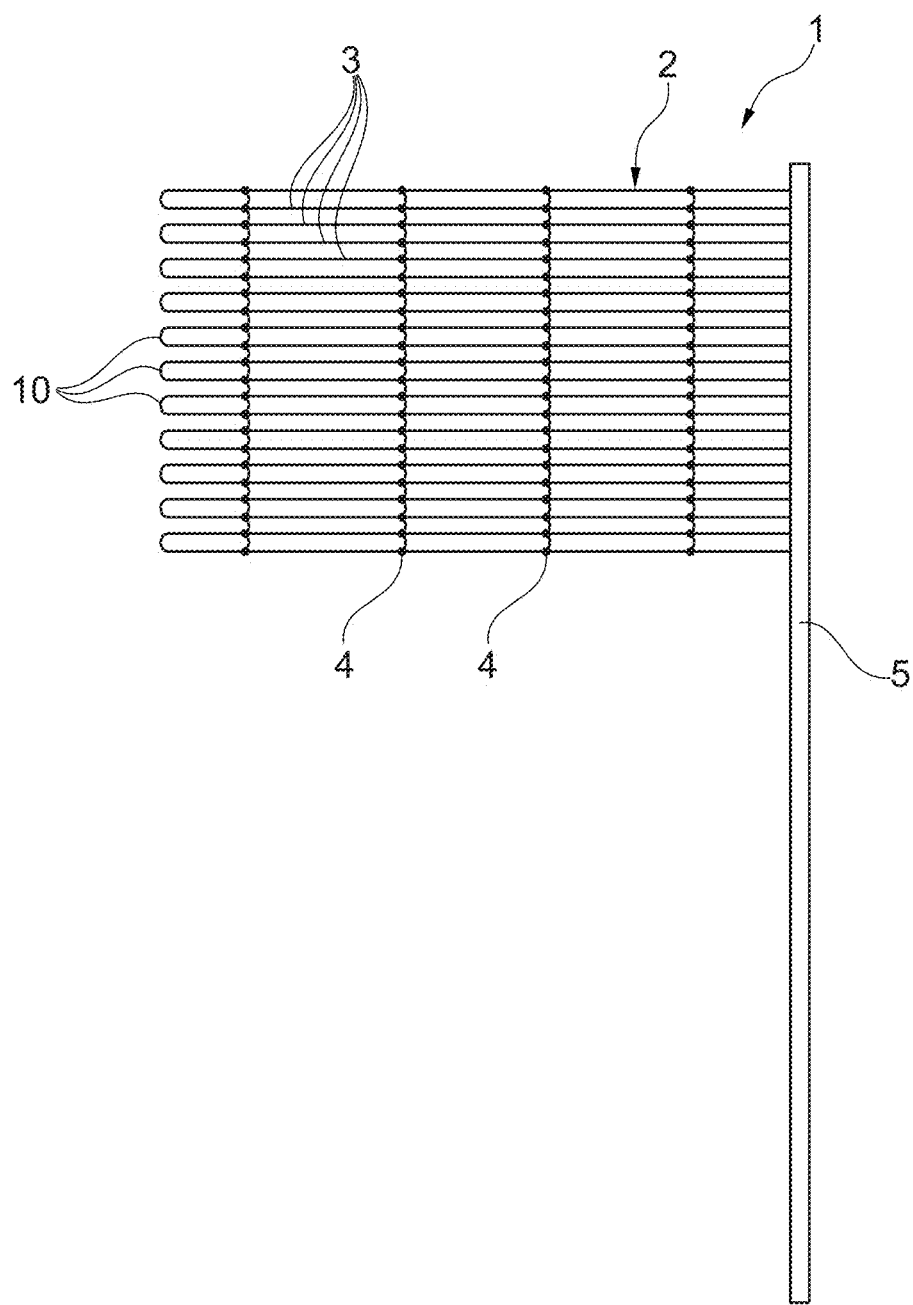
Figure 4:
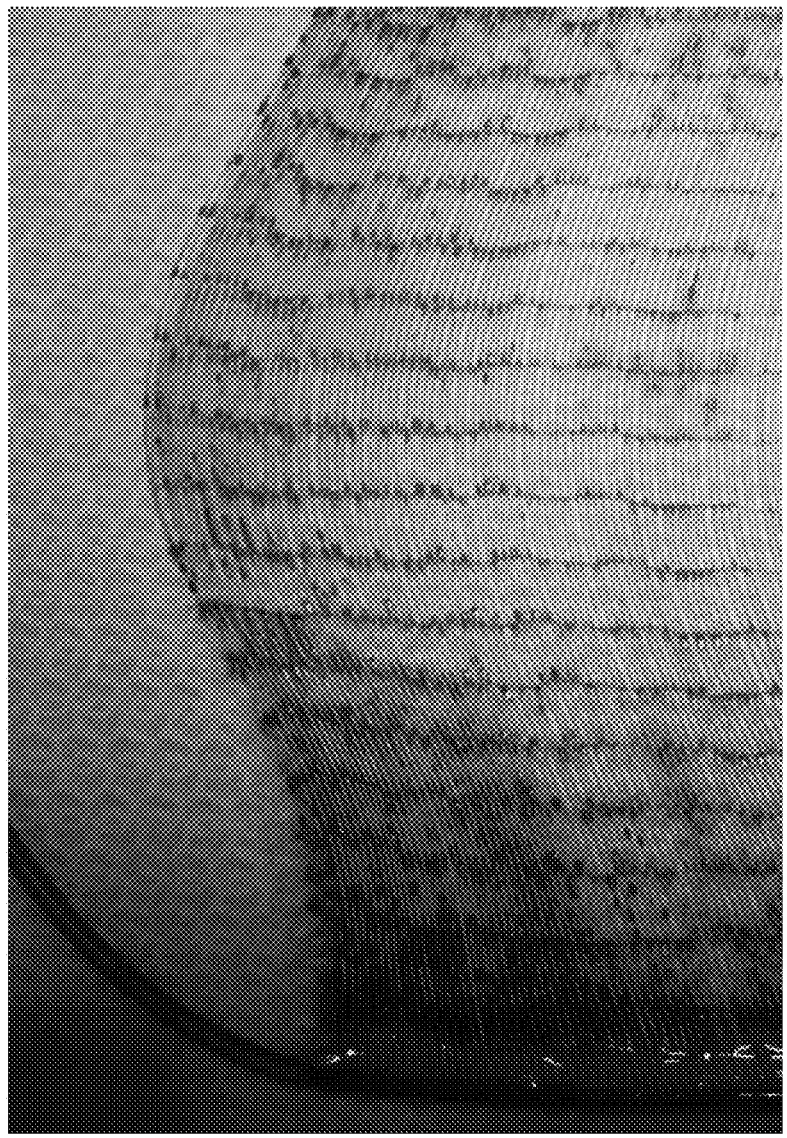

The invention is further explained by means of the following figures, wherein the scope of the invention is not limited by the figures:

The following is shown:

FIG. 1: a wound care system having a single-layer mat made of capillary membranes and supply lines at both ends of the mat FIG. 2: a wound care system having a supply line at one end of the mat and sealed capillary membrane ends at the opposite end of the mat FIG. 3: a wound care system having a supply line at one end of the mat and U-shaped capillary membrane ends at the opposite end of the mat FIG. 4: a photographic image of a portion of a wound care system according to the invention having a single-layer arrangement of mutually parallel capillary membranes during a test with a simulation solution FIG. 1 shows, schematically and not to scale, a plan view of a wound care system 1 according to the invention having a single-layer arrangement 2 of capillary membranes 3. The capillary membranes 3 are connected to one another to form a mat by means of mutually parallel connection elements 4 so as to be mutually parallel and held at a distance from one another. In the present example, the capillary membranes 3 are embedded in supply lines 5, 6 with their opposite ends in such a way that a fluid connection exists between the lumen of the supply lines 5, 6 and the lumen of the capillary membranes 3. The supply lines 5, 6 are combined to form a common line 8 via a Y-piece 7. From this construction, it follows that a nutrient solution, for example, which is fed via the line 8, is distributed to the supply lines 5, 6 and fed to the capillary membranes 3 in the dead-end mode. The nutrient solution flows through the porous, semi-permeable walls of the capillary membranes 3, out of these and is fed uniformly to the wound across the area of the arrangement 2 of capillary membranes 3, wherein, for uniform distribution, the conditions according to the invention, both with regard to the distance of the capillary membranes 3 from one another and with regard to the distance of the connection elements from one another must be adhered to.

FIG. 2 likewise shows, schematically and not to scale, a wound care system 1 having a single-layer arrangement 2 of capillary membranes 3 in which the capillary membranes 3 are embedded in a supply line 5 with only one of their ends. The second, opposite ends of the capillary membranes 3 are enclosed, e.g. by means of a silicone material 9, and are thus closed. The capillary membranes 3 are likewise connected to one another by means of mutually parallel connection elements 4 to form a mat so that they are mutually parallel and held at a distance from one another.

A wound care system 1, as depicted in FIG. 2, is generally appropriate for smaller widths, so that, despite the mat of capillary membranes 3 being supplied from only one side, e.g. with a nutrient solution, the nutrient solution is at least substantially homogeneously distributed on the wound to be treated across the width of the mat.

FIG. 3 likewise shows, schematically and not to scale, a wound care system 1 in which the capillary membranes 4 are connected to only one supply line 5. In contrast to the mats of capillary membranes shown in FIG. 2, the capillary membranes here are open at both of their ends and embedded in a supply line 5 with both of their ends. The free ends 10 of the capillary membranes 3 are designed to be U-shaped at the end of the mat opposite the supply line 5, and thus closed there. In this way, the inflow takes place in the dead-end mode in the capillary membranes 3 of the wound care system 1 shown in FIG. 3, as well.

FIG. 4 shows a photographic image of a segment of a wound care system according to the invention having a single-layer arrangement of mutually parallel capillary membranes during a test with a simulation solution. The segment shown is part of a mat with dimensions of 200 mm in the longitudinal direction (in the direction of the capillary membranes) and 200 mm in the transverse direction (in the direction transverse to the capillary membranes), consisting of capillary membranes of the MicroPES® TF10 type (Membrana GmbH), which, in the segment shown, runs partially in an arch in the vertical direction. The capillary membranes are connected to form a knitted mat via connection elements in the form of multifilament polyester fibers, the polyester fibers running in the horizontal direction. The polyester fibers are at a distance of 5 mm from one another; the distance of the capillary membranes from one another is about 2.7 times the external diameter of the capillary membranes (500 µm). The capillary membranes are embedded with one of their ends in a supply line, which can be seen at the lower edge of the image.

The photographic image of FIG. 4 shows a snapshot at the beginning of a test to study the homogeneity of the distribution of a liquid fed over the capillary membrane mat. A colored safranin solution was used as a model liquid. At the early stage of the experiment, the distribution of the liquid via the capillary membranes begins at the supply line at the lower part of the mat. However, it can be clearly seen that, already at this early stage, distribution of the liquid also originates from the intersections of the capillary membranes with the polyester fibers, which is clearly visible in FIG. 4 in the dark points or lines across the area of the mat. The discharge of liquid from the capillary membranes and, simultaneously, the homogeneous distribution of the liquid over the area across the intersections of the capillary membranes with the connection elements is thus favored.

The invention claimed is:

1. Wound care system, comprising a single-layer arrangement of mutually parallel capillary membranes with a porous, semi-permeable wall and a lumen and at least one open end,
    wherein the capillary membranes have an external diameter in the range of 50 to 500 µm and a wall thickness in the range of 5 to 1000 µm,
    wherein the capillary membranes, with their at least one open end, are connected to at least one common supply line with a wall and a lumen,
characterized in that
    the capillary membranes, with their at least one open end, are embedded at their outer periphery so fluid-tightly in the wall of the at least one supply line that a fluid connection exists between the lumen of the supply line and the lumen of the capillary membranes,
    the arrangement of mutually parallel capillary membranes furthermore has a plurality of spaced and mutually parallel connection elements by means of which the capillary membranes are connected to one another to form a mat and are held at a distance from one another by the connection elements wherein the connection elements are thread-like;
    the distance of the capillary membranes from one another in the mat is 1 to 10 times the external diameter of the capillary membranes, wherein the distance is measured from the longitudinal axes of the capillary membranes, and
    the distance of the connection elements from one another lies in the range of 1 to 50 mm.

2. The wound care system according to claim 1, characterized in that the capillary membrane arrangement is connected to two supply lines, wherein the capillary membranes are each embedded with their opposite ends in a respective supply line.

3. The wound care system according to claim 1, characterized in that the capillary membranes have a transmembrane flow for water in the range of 0.01 to 50 mL/(min·cm²·bar).

4. The wound care system according to claim 1, characterized in that the thread-like connection elements are connecting fibers.

5. The wound care system according to claim 4, characterized in that the connecting fibers are multifilament polyester threads, polypropylene threads or polytetrafluoroethylene threads.

6. The wound care system according to claim 4, characterized in that the mat is a woven mat in which the capillary membranes and the connecting fibers are woven together.

7. The wound care system according to claim 4, characterized in that the mat is a knitted mat, in which the capillary membranes and the connecting fibers are knitted together.

8. The wound care system according to claim 1, characterized in that the at least one common supply line is a flexible silicone tube.

9. The wound care system according to claim 1, characterized in that it comprises at least one additional arrangement of capillary membranes.

* * * * *